(12) United States Patent
Dick et al.

(10) Patent No.: US 6,726,679 B1
(45) Date of Patent: Apr. 27, 2004

(54) METHOD AND DEVICE FOR TREATING OPAQUENESS AND/OR HARDENING OF A CLOSED EYE

(75) Inventors: Manfred Dick, Gefell (DE); Eckhard Schroeder, Eckental (DE)

(73) Assignee: Asclepion Meditec AG, Jena (DE)

( * ) Notice: Subject to any disclaimer, the term of this patent is extended or adjusted under 35 U.S.C. 154(b) by 0 days.

(21) Appl. No.: 10/069,607

(22) PCT Filed: Aug. 25, 2000

(86) PCT No.: PCT/EP00/08308
§ 371 (c)(1),
(2), (4) Date: Feb. 25, 2002

(87) PCT Pub. No.: WO01/13838
PCT Pub. Date: Mar. 1, 2001

(30) Foreign Application Priority Data

Aug. 26, 1999 (DE) .......................................... 199 40 712

(51) Int. Cl.[7] .............................................. A61F 9/008
(52) U.S. Cl. ................. 606/4; 606/6; 128/898
(58) Field of Search ............................ 606/4–6; 128/898

(56) References Cited

U.S. PATENT DOCUMENTS

| 4,907,586 A | * | 3/1990 | Bille et al. ................ 606/5 |
|---|---|---|---|
| 5,741,245 A |   | 4/1998 | Cozean et al. ............. 606/5 |
| 6,197,018 B1 | * | 3/2001 | O'Donnell, Jr. ........... 606/4 |
| 6,258,082 B1 | * | 7/2001 | Lin ........................... 606/5 |
| 6,322,556 B1 | * | 11/2001 | Gwon et al. ............... 606/6 |
| 6,325,792 B1 | * | 12/2001 | Swinger et al. ........... 606/4 |
| 6,482,199 B1 | * | 11/2002 | Neev ....................... 606/10 |
| 2002/0013574 A1 |   | 1/2002 | Elbrecht et al. .......... 606/5 |

FOREIGN PATENT DOCUMENTS

| DE | 19718139 | 11/1998 |
|---|---|---|
| WO | 9308677 | 5/1993 |
| WO | 9425107 | 11/1994 |

* cited by examiner

Primary Examiner—Roy D. Gibson
Assistant Examiner—Henry M. Johnson, III
(74) Attorney, Agent, or Firm—Davidson, Davidson & Kappel, LLC

(57) ABSTRACT

The present invention relates to a method and a device for treating opacities and/or hardenings of an unopened eye.

It is a specific advantage of the solution according to the invention that the treamtment of the inner region of the eye is possible without the need to introduce a surgical instrument into the eye.

24 Claims, 3 Drawing Sheets

METHOD AND DEVICE FOR TREATING OPAQUENESS AND/OR HARDENING OF A CLOSED EYE

BACKGROUND OF THE INVENTION

The present invention relates to a method and a device for treating opacities and/or hardenings of an unopened eye. Specifically, the present invention relates to a laser system and a method for cleaning, in particular, the ageing human eye from gray hazes in the cornea, the lens or the vitreous body to restore transparency in the eye.

In ophthalmology, it is known that, in particular in the ageing eye, opacities develop in the lens (cataract) or in the vitreous body or the cornea. At the advanced stage, the treatment is presently limited to replacing the lens with a plastic lens during a cataract surgery, replacing the vitreous body with silicone oil by vitrectomy, or also to transplanting the cornea. It is known to carry out the surgery of the cataract and the vitrectomy of the vitreous body using a laser. During a surgery, the laser beam is in both cases led directly to the tissue to be treated. A proven efficient laser is, in particular, the Er:YAG laser having the emission wavelength of 2.94 μm whose radiation is strongly absorbed by water. For conveying the laser radiation, cannulas with optical waveguides are led up to the location of treatment. Although cannulas having diameters of approximately 1 mm are manufacturable now, the necessity of the surgical intervention remains. A device for carrying out a laser phacoemulsification is described, for example, in German Patent 19718139.

Also known are surgical techniques in the case of which the eye is not opened but the laser light is guided into the eye via the normal path of the visual process. These techniques include the possibility of attaining an optical disruption inside of the cornea by focusing fs laser pulses (300 fs, 1 μJ, 780 nm), resulting in the formation of blisters. By folding open a lamella, it is possible to prepare an intrastromal lenticle whose removal brings about a refractive correction. It is known, moreover, that the gray after-cataract membrane can be disruptively removed with the aid of ns pulses of a Q-switched Nd:YAG laser.

In known methods heretofore, apart from medicamentous methods, it was not possible to treat the clouded regions already at the initial stage. Thus, the known laser techniques are not suitable for removing the clouded regions in the eye without opening the eye. Therefore, it is an object of the present invention to provide a method and a device which make it possible to dissolve clouded regions in the eye.

A further phenomenon which occurs in old age is presbyopia. One reason for this lies in the hardening of the lens, which can occur, for example, due to deposit of substances. Apart from the utilization of spectacles, photorefractive keratectomy (PRK) has often been used recently for correcting the visual defect. Removal of the hardening itself has not been possible in known methods heretofore. Therefore, it is a further object of the present invention to provide a device with which the lens' ability to contract is increased again.

SUMMARY OF THE INVENTION

Therefore, it is an object of the present invention to provide a method and a device which make it possible to dissolve opacities and/or hardenings of an eye.

This objective is achieved, in particular, by a method for dissolving opacities and/or hardenings of an unopened eye in connection with which the opacities and/or hardenings are dissolved via at least one ultrashort pulse of a laser without opening the eye. By using an ultrashort pulse which is sent through the transparent eye structure, no thermal or athermal damage is produced on the retina or other uninvolved regions. In the working plane (for example, the lens, the vitreous body or in the cornea), there exists an energy density of such a kind that indeed nothing happens in the fully transparent medium of the eye but that disruptions are induced at heterogeneous spots of clouding by local absorption, the disruptions dissolving these impurities. These disruptions result in the evaporation of these impurities.

The gas blisters (cavities) possibly forming in the process are filled up in a few hours and disappear in this manner. The dissolved impurities are reduced by resorption and/or dispersion, or disappear completely.

Pulses which lie in the ps range are preferably used as ultrashort pulses; particular preference being given to pulses which lie in the fs range. It is preferred to use pulses of from 10 ps to 10 fs, particularly preferably of 300 fs.

The special advantage of the method according to the present invention lies in that the opacities and/or hardenings of the eye can be removed or reduced without having to open the eye. In this manner, the risks involved in surgery are avoided. Using the method according to the present invention, moreover, a treatment which is more gentle and carried out in small steps can be accomplished by appropriate selection of the energy of the ultrashort pulse.

It is preferred for the ultrashort pulses to be further amplified, particularly preferably via the Chirped Pulse Amplification Method (CPA method).

In a preferred method according to the present invention, the opacities and/or hardenings are dissolved with the assistance of a pulse train having a duration of less than 5 s, preferably less than 3 s, particularly preferably less than 0.1 s of the ultrashort pulses. It is very particularly preferred to provide pulse lengths in the range of from 10 ps to 10 fs, and especially preferably of approximately 300 fs. The energy input in the region to be treated can be predetermined via the selection of a pulse train by determining the duration. By selecting extremely short pulse trains, it is possible, moreover, to prevent efficiency losses which could occur, for example, because of a movement of the eye during the treatment. The pulses particularly preferably have a duration of less than 10 ps. It is also conceivable to use the pulse train in continuous operation until the desired effect has been attained. Very particularly preferably, it is also possible to use single pulses and very short pulse trains to achieve a particularly gentle treatment by iteratively monitoring the success of treatment.

In a further preferred method of the present invention, pulse trains with a repetition frequency, in particular, with a repetition frequency in the kHz range are emitted. In this connection, the pulse trains themselves are superposed with a repetition frequency once again. In this manner, the energy input into the region to be treated can be varied over time once more in spite of the selection of a longer pulse train or even of a continuous operation. Because of this, an even more gentle treatment is possible, avoiding any thermal or athermal damage to the eye in regions which are not intended to be treated.

In a further preferred method of the present invention, one chooses a laser radiation of a wavelength distribution which has a higher absorption and/or a lower reflection for the opacities and/or hardenings than for the remaining parts of the eye. In this manner, it is possible to adjust the energy density in such a manner that the density required for triggering an optical breakdown is only reached at locations of local absorption. This selective adjustment is attained through the increased absorption of the opacities and/or hardenings at the selected wavelengths. It is particularly preferred to chose a laser for whose wavelength the eye is highly transmissive. The wavelength is preferably 350 to 1300 nm. It is particularly preferred to chose a laser to whose radiation the sensitive regions such as the retina or the macula are somewhat less sensitive. This can be accomplished via a lower absorptivity of these regions in the eye for the selected radiation. This can also be achieved by a higher reflectivity of the regions of the eye which are not to be treated. Thus, the radiation cannot cause any damage in the regions of the eye which are not to be treated just because of the absorptive and reflective behavior, independently of the energy density which can be generated by focusing.

In a further preferred method of the present invention, ultrashort pulses are aligned in such a manner that energy densities which dissolve the opacities and/or hardenings occur within the opacities and/or hardenings while, at the same time, no damage is caused to the tissue in the sensitive region of the eye. Apart from the selection of the wavelength, this can be accomplished by a focusing of the beam and a corresponding beam guidance of the pulses. Thus, by shaping the beam geometry of the pulse, it is possible to couple in energy densities in the region of the tissue to be treated which give rise to a disruption (and, consequently, to the dissolution) of the pathological (less transparent) tissue. At the same time, the beam can be shaped in such a manner that, in the area of sensitive regions such as the retina and, in particular, the macula, energy densities occur which do not result in the destruction of this tissue.

This can preferably be attained via the beam guidance in that, upon passage of the beam through the target region to be treated, the beam is widened in such a manner that the energy densities in the sensitive region are so low that the region cannot be damaged. In a further preferred method, the complete eye lens or a region thereof having a preselected size is irradiated with a converging beam of rays and an energy density in the region of the lens below that of the optical breakdown. In the process, the focus lies in the vitreous body. On the other hand, the energy is selected such that, given transparency of the lens, an optical breakdown occurs at the focus in the vitreous body. Since all the energy is consumed during the optical breakdown at the focus, it is possible to provide a high level of treatment safety with regard to the macula. Any possible formation of blisters in the vitreous body will relax after a short time.

In a further preferred method of the present invention, the alignment of the ultrashort pulses takes place via a deflection device and/or focusing optics and/or a contact glass. This makes it possible not only to accurately align the ultrashort pulses and the thereby described beam with the region to be treated but also to preselect the energy density which is desired in the target region. By drawing upon known devices, it is possible for the method according to the present invention to be implemented in cost-effective manner.

In another preferred method of the present invention, data on the opacities and/or hardenings is acquired by measuring reflected radiation of low energy prior to the actual treatment, this acquired data being taken into account in the selection of the alignments of the energy of the pulses to be used. To protect the sensitive regions, in fact, it lies especially also within the scope of the present invention to irradiate with considerably lower intensities which are harmless to the eye prior to the actual therapeutic radiation, and to draw conclusions on the alignment of the laser and on the radiation dose required in the specific radiation direction on the basis of the radiation which is reflected, for example, at the opacities. Since the energy of the radiation is substantially used up during the disruption of opacities, optimum adaptation of the beam geometry to the opacities to be treated is also advantageous for the gentle treatment of the sensitive regions. The thus acquired data permits individual and well-directed treatment of the identified regions. In particular, this data can also be acquired between the individual treatment steps to ascertain the extent of success the treatment has shown so far. Thus, it is possible, for example, to sent a low-energy signal after an ultrashort pulse or a pulse train to obtain data therefrom on the changes caused by the ultrashort pulse or pulse train in the region to be treated.

In a further method according to the present invention for treating the presbyopia of an eye, blisters are produced in the lens of the eye, and these blisters are filled with liquid without having to open the eye. This formation of blisters inside of the lens gives rise to a loosening of the lens material. The blisters formed in this manner are automatically filled with liquid again. Because of these blisters filled with liquid, a lens is produced which has a higher flexibility than the original lens. However, the accommodation of the lens is thereby increased.

It is particularly preferred for the blisters to be produced as blister fields in the marginal area of the lens. This placing of blisters in the marginal area or in the marginal zone of the lens results in a softening of the lens upon filling with liquid. This brings about a higher flexibility and, thus, a higher accommodation of the lens. Via a symmetrical arrangement of the blister fields, it is possible for the accommodative capacity of the lens to be preserved symmetrically. In the case that the lens is hardened only partially, then the flexibility of the lens can be increased in a particular region by selective formation of blisters. In this manner, it is possible to improve the overall symmetry of the lens during accommodation.

The object of the present invention is achieved, moreover, by a device for treating opacities and/or hardenings of an unopened eye, including a laser having a frequency distribution in the range of from 350 nm to 1300 nm as well as a device for generating ultrashort pulses, provision being made for a device for aligning the ultrashort pulses, including a deflection device and/or focusing optics and/or a contact glass, provision being made for a control device via which the device for aligning the ultrashort pulses is controlled as a function of data on the opacities and/or hardenings. Using this device, it is possible to accomplish the above advantages of the method according to the present invention. The optical means for coupling in the radiation are preferably constituted by tunable focusing optics, deflection mirrors of a micromanipulator, contact glasses, special mirror contact glasses and surgical microscopes or slitlamps. Using these elements, it is possible for the beam to be set up and aligned inside of the eye in such a manner that the energy input can be predetermined very precisely in the regions to be treated without the possibility that an energy density might occur outside of these regions to be treated which is detrimental for the tissue existing there. In a further preferred exemplary embodiment of the present invention, provision is made for a control device via which the device for aligning the ultrashort pulses can be controlled, particularly preferably as a function of data on the opacities and/or hardenings. Using this control device, the data which has been ascertained on the regions to be treated can be prepared in such a manner that the pulse duration, sequence, and the energy density to be introduced can be determined and that the device for aligning the ultrashort pulses can be set up and aligned via the control device on the basis of the determined parameters by adjusting the individual elements of the optical system via the control device in such a manner that the desired region can be treated with the predetermined energy input. The laser is selected such that it canlemit pulses in the ps range, preferably in the fs range.

In a further refinement, the laser as coherent light source includes a device for generating at least one pulse train. This pulse train has preferably a duration of less than 5 s, especially preferably less than 2 s and, particularly preferably, of less than 0.1 s. It is particularly preferred to provide pulse lengths in the range of from 10 ps to 10 fs and, very particularly preferably, pulse lengths of approximately 300 fs. The device according to the present invention is preferably also able to provide pulse trains in continuous operation or to emit single pulses. Using the device for generating pulse trains with a repetition frequency, particularly preferably in the kHz range, of the laser as coherent light source, it is possible to produce the superposition of the individual pulse trains with the repetition frequency described in the method according to the present invention, increasing the gentle introduction of the energy into the region to be treated.

The coherent light source particularly preferably features a device for generating a laser radiation having a frequency distribution which has a higher absorption and/or a lower reflection for the opacities and/or hardenings than for the remaining parts of the eye. For that purpose, it is particularly preferred to use a tunable laser which is able to radiate in the range of from 350 nm to 1300 nm. It is particularly preferred to provide a laser which is able to radiate in the range of 780 nm, such as a Ti-sapphire laser or, also preferably, in the range of 1060 nm, such as an Nd:glass laser. Using such a laser, it is possible to attain the advantages of the method according to the present invention.

The object is achieved according to the present invention by using a device or method according to the present invention for the treatment of haze formation in the cornea subsequent to excimer laser treatments, in the case of cloudings of the lens nucleus, in the case of incipient cataract and/or for impurities of the vitreous body in the visual field.

BRIEF DESCRIPTION OF THE DRAWINGS

In the following, exemplary embodiments of the present invention and advantageous refinements will be explained in greater detail on the basis of drawings. In this context.

DETAILED DESCRIPTION

Figure 1:
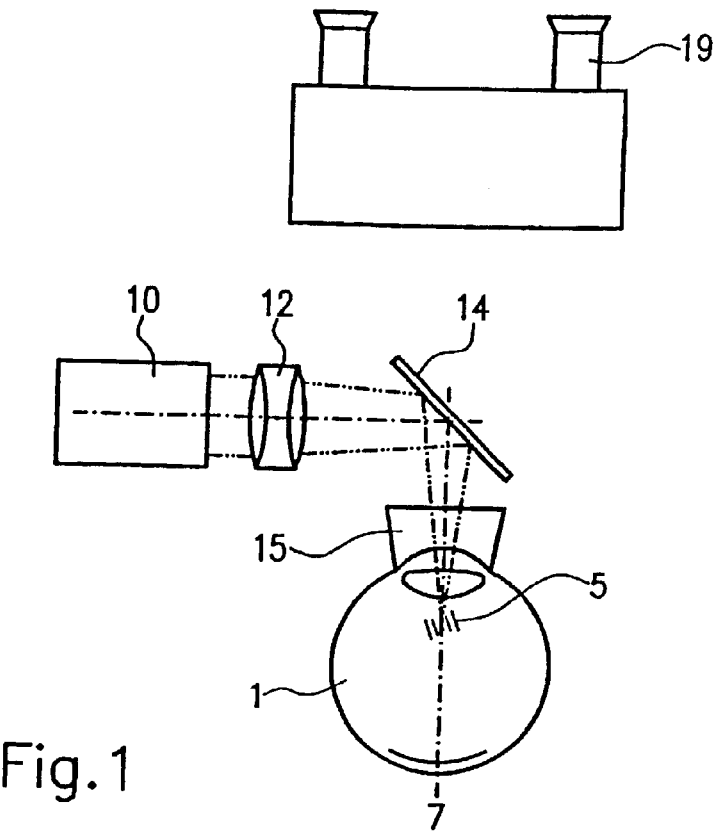
FIG. 1 shows an exemplary embodiment of the device according to the present invention for treating an opacity in the visual field of the vitreous body.

FIG. 1 shows a first exemplary embodiment of the present invention for treating an opacity in the vitreous body in the visual field directly behind the lens. Focusing optics 12 are connected downstream of a laser 10, here a mode-locked laser. A deflection mirror with micromanipulator 14 is arranged downstream of the focusing optics. A contact glass 15 is placed on the eye 1 to be treated. A clouded region 5 is situated downstream of the eye lens. A surgical microscope with slitlamp 19 is used for monitoring.

The mode-locked laser system is used to generate ultrashort laser pulses, preferably of 10 ps to 10 fs, which are further amplified using the Chirped Pulse Amplification Method to make available pulse energies above 1 mJ in the kHz range. At the wavelength of 780 nm (Ti-sapphire) or 1060 nm (Nd:glass), the transparent regions of the cornea, lens or vitreous body to be treated have a low absorption which are not damaged when irradiated with sufficiently low energy densities of the ultrashort pulse. A focusing device 12 which is used for aligning and focusing the beam is arranged downstream of laser 10. The beam is focused via deflection mirror with micromanipulator 14 through contact glass 15 onto clouded region 5.

During operation, the laser emits pulse trains 25 of ultrashort pulses 20. These are only absorbed by the pathological clouded regions whereby a selective treatment is rendered possible. In the process, the ultrashort pulses result in a locally limited, disruptive size reduction process of the clouded tissue without detrimental thermal side effects. Upon the filling of the induced blisters, the local, selective and athermal size reduction process restores transparency in this region. Possibly developing cavitations in the vitreous body are refilled with liquid by the body within a short time. In this manner, region 5 becomes transparent again after the treatment.

Given an appropriate selection of energy, it is also possible to treat clouded regions in the eye lens using this arrangement. In this connection, the energy is selected such that the transparent parts of the eye lens do not permit absorption of the selected wavelength. The clouded regions in the eye lens, however, absorb the radiation and thus, the ultrashort pulses give rise to a locally limited, disruptive size reduction process of the clouded tissue also in the eye lens without detrimental thermal side effects. The energy which were not absorbed by the clouded regions are used up by disportion at the focus in the vitreous body and, consequently, cannot damage the retina. The cavitations developing the vitreous body are refilled the liquid of the body within a short time and, consequently, are transparent again.

Figure 2:
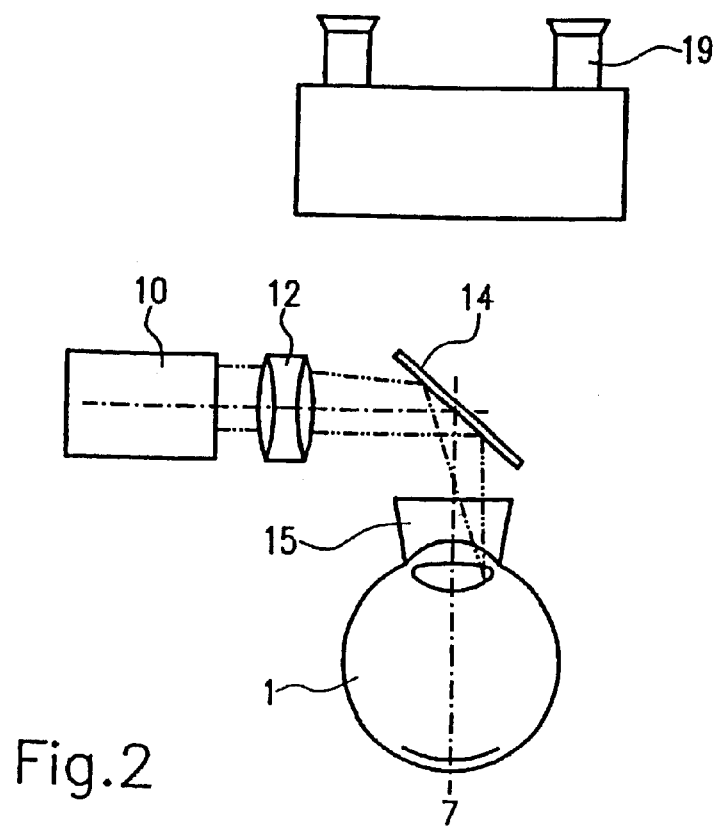
FIG. 2 depicts an exemplary embodiment of the present invention for treating presbyopia.

FIG. 2 depicts an exemplary embodiment of the present invention for treating presbyopia. The device corresponds essentially to that in FIG. 1. However, the beam deflection of the pulse train takes place via deflection mirror with micromanipulator 14 in such a manner that the focus comes to rest in the marginal area of the lens. According to the present invention, the blisters can thus be produced preferably in the marginal area of the lens which, upon filling with preferably endogenous fluid, have a higher flexibility and therefore accommodative capacity. In this manner, it is possible to place whole fields of blisters, resulting in a regional softening of the lens and, consequently, in a corresponding increase in flexibility.

Figure 3:
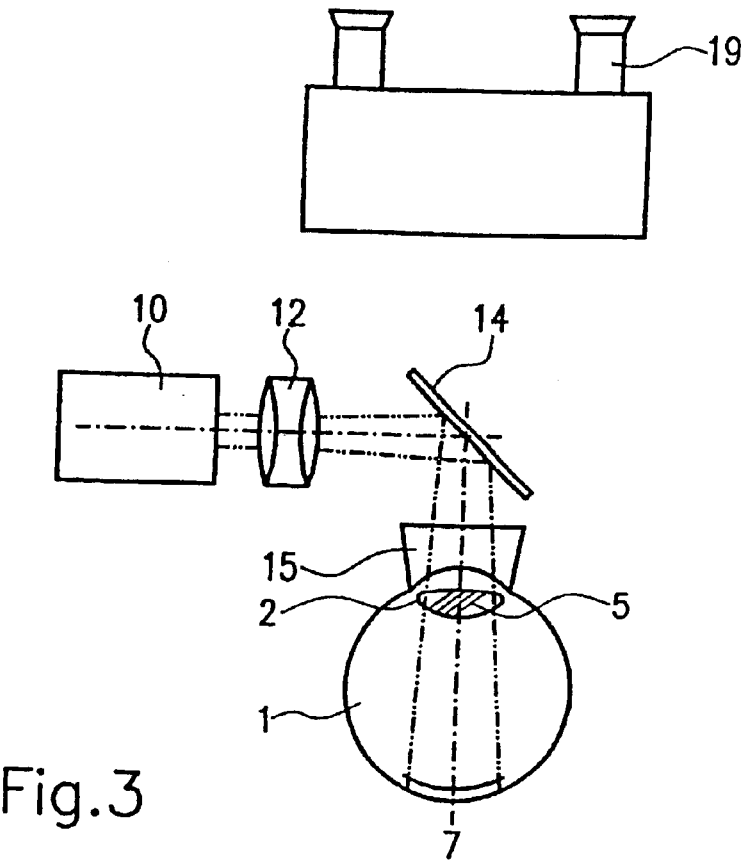
FIG. 3 depicts a further exemplary embodiment of the present invention for treating the eye lens.

FIG. 3 depicts another exemplary embodiment of the present invention for treating the eye lens. This exemplary embodiment also corresponds to that shown in FIG. 1 in its essential design. Via optical system 12 used here, however, the beam is widened in such a manner that it can be adjusted in the area of eye lens 2 so as to produce an energy input here which results in a destruction of clouded regions 5 in lens 2 while, in its further course, the beam is widened in such a manner that the energy in the area of macula 7 is so low that no damage can be caused to the tissue here.

Via special divergent beam guidance and appropriate irradiation as well as possible automated scanning methods, the radiation is guided during the treatment in such a manner that neither the retina nor any locations other than the pathological ones can be damaged.

Figure 4:
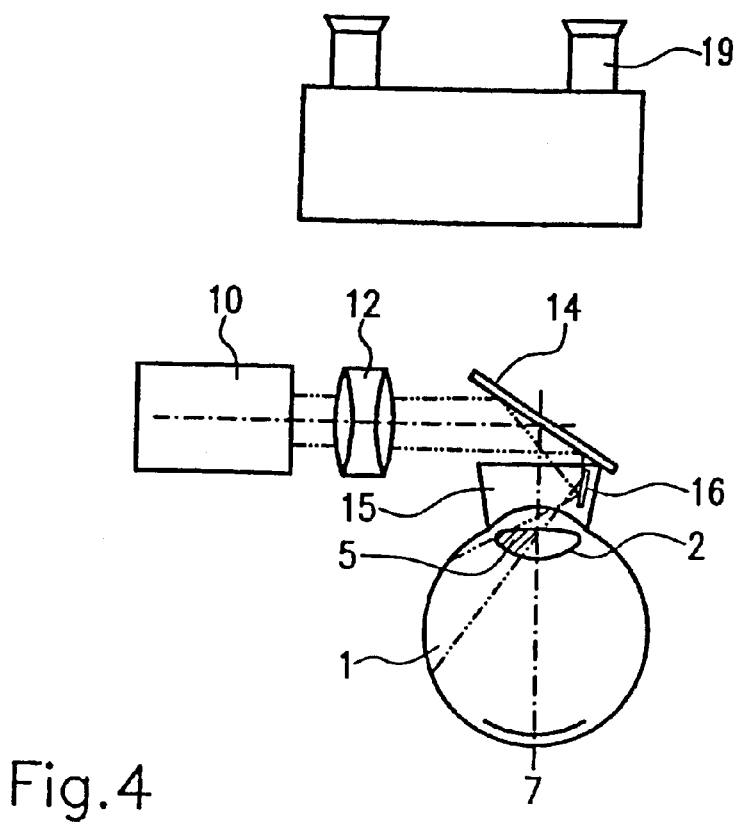
FIG. 4 shows a further exemplary embodiment of the present invention for treating a particular region of the eye lens.

FIG. 4 is a another exemplary embodiment of the present invention for treating a particular region of eye lens 2. In this context, a mirror 16 is provided in contact glass 15, the mirror making it possible for the pulse train to be aligned with a particular region of the eye lens. The beam impinges on deflection mirror with micromanipulator 14 which sets up the beam through contact glass 15 onto mirror 16 in contact glass 15, the mirror 16 aligning the beam with the area of eye lens 2 in which clouded region 5 exist.

Figure 5:
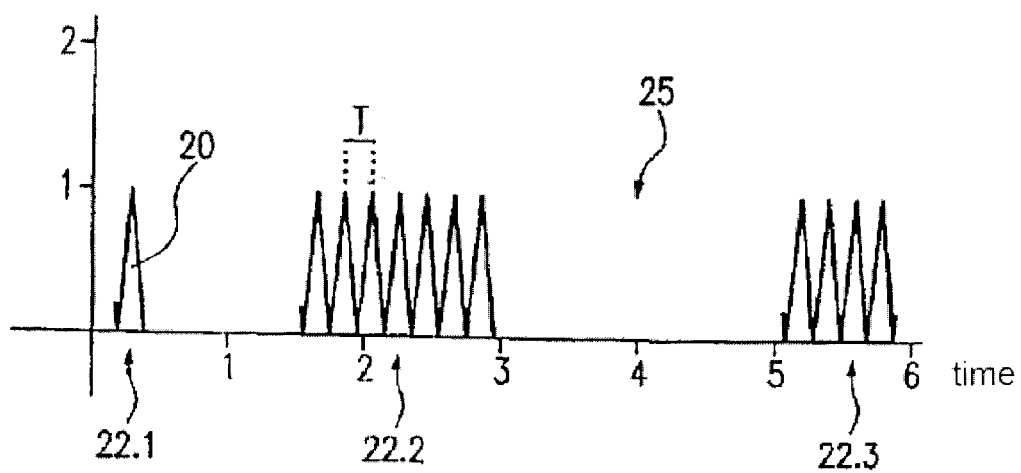
FIG. 5 is a diagram of a pulse train with a representation of the time axis and amplitude.

FIG. 5 shows a diagram of a pulse train 25 with a representation of the time axis and amplitude. The individual ultrashort pulses 20 have a width of several femto-seconds. Pulse train 25 is formed of three pulse bursts 22 of different lengths 22.1, 22.2 and 22.3, and superposed with a frequency sequence having the period T. In this manner, the energy input via the ultrashort pulses can be further varied. While time t is represented on the x-axis, amplitude A is indicated on the y-axis. In lieu of a frequency sequence in the kHz range, a linear or a quasi-linear rising envelope or falling envelope can also be thought of. First pulse burst 22.1 is constituted by one single pulse 20. Pulse train 22.2 is constituted by several single pulses which, in turn, are spaced from one another by time T. T usually lies in the ms range while the width of single pulses 20 lies in the fs range. Pulse train 25 is formed of the pulse bursts together with pulse burst 22.3.

According to the present invention, a method at and a device for treating opacities and/or hardenings of an unopened eye was introduced. A special advantage of the design approach according to the present invention is that it enables treatments to be carried out inside the eye without having to introduce a surgical instrument into the eye.

List of Reference Symbols 1 eye
2. lens
3. vitreous body
4. cornea
5. opacities
7. macula
10. laser
12. optical system (focusing optics)
14. deflection mirror with micromanipulator
15. contact glass
16. mirror in the contact glass
19. surgical microscope with slitlamp
20. ultrashort pulse
22. pulse burst
25. pulse train

What is claimed is:

1. A method for noninvasively dissolving opacities and/or hardenings of an eye comprising:
    dissolving at least one of an opacity and a hardening via a plurality of ultrashort pulses of a laser defining a pulse train having a duration of less than 1 s.
2. The method as recited in claim 1, wherein the duration is less than 0.1 s.

3. The method as recited in claim 1, wherein the pulse train is emitted repeatedly.
4. The method as recited in claim 3, wherein a repetition frequency of the repeated pulse train is in the kHz range.
5. The method as recited in claim 1, further comprising
    selecting a laser radiation of a wavelength which has at least one of a higher absorption and a lower reflection for the at least one of the opacity and the hardening than for a remaining part of the eye.
6. The method as recited in claim 1, further comprising aligning the ultrashort pulses so that energy densities which dissolve the at least one of the opacities and hardenings occur within the at least one of the opacity and the hardening while, at the same time, no damage is caused to tissue in other regions of the eye.
7. The method as recited in claim 6, wherein the alignment of the ultrashort pulses takes place via at least one of a deflection device, focusing optics and a contact glass.
8. The method as recited in claim 1, further comprising
    acquiring data on the at least one of the opacity and the hardening by measuring reflected radiation of low energy prior to actual treatment, and
    selecting the alignment and the energy of the ultrashort pulses as a function of the acquired data.
9. A method for operating a device according to claim 1, the method comprising:
    using the device subsequent to an excimer laser treatment in the case of haze formation in the cornea.
10. The method for operating a device according to claim 1, the method comprising using the device to treat cloudings of a lens nucleus in the case of incipient cataract.
11. The method for operating a device according to claim 1, the method comprising using the device to treat impurties in a vitreous body in a visual field.
12. A method for noninvasively treating the presbyopia of an eye comprising
    using the method of claim 1, and producing blisters in a lens of the eye, the blisters filling with liquid.
13. The method as recited in claim 12, wherein the blisters are produced as blister fields in the lens.
14. A device for noninvasively treating opacities and/or hardenings of an eye comprising:
    a laser having a wavelength in a range of from 350 nm to 1300 nm; and
    a device for generating a pulse train of ultrashort pulses from the laser, the pulse train having a duration of less than 1 s,
    an aligning device for aligning the ultrashort pulses, the aligning device including one of a deflection device, focusing optics, and a contact glass, and
    a control device controlling the aligning device for aligning the ultrashort pulses as a function of data on at least one of the opacity and the hardening.
15. The device as recited in claim 14, wherein the duration of the pulse train is less than 0.1 s.
16. The device as recited in claim 14, wherein the device for generating a pulse train generates pulse trains with a repetition frequency.
17. The device as recited in claim 16, wherein the device for generating pulse trains with a repetition frequency generates pulse trains in the kHz range.
18. The device as recited in claim 14, further comprising a device for generating a laser radiation having a wavelength which has at least one of a higher absorption and a lower reflection for the at least one of the opacity and the hardening than for remaining parts of the eye.

19. The device as recited in claim 14, wherein the wavelength of the laser is in the range of from 780 nm to 1060 nm.

20. A method for noninvasively dissolving opacities and/or hardenings of an eye comprising:

dissolving at least one of an opacity and a hardening via a plurality of ultrashort pulses of a laser defining a pulse train, wherein the pulse train is emitted repeatedly and wherein a repetition frequency of the repeated pulse train is in the kHz range.

21. The method as recited in claim 20 wherein the method is used for treating a haze formation subsequent to an excimer laser treatment.

22. The method as recited in claim 20 wherein the method is used for treating cloudings of a lens nucleus in the case of an incipient cataract.

23. The method as recited in claim 20 wherein the method is used for treating impurities in a vitreous body in a visual field.

24. A method for noninvasively treating the presbyopia of an eye comprising:

dissolving at least one of an opacity and a hardening via a plurality of ultrashort pulses of a laser defining a pulse train so as to produce blisters as blister fields in a lens of the eye, the blisters filling with liquid.

* * * * *